United States Patent
Abe

(10) Patent No.: US 8,253,785 B2
(45) Date of Patent: Aug. 28, 2012

(54) VIDEO SIGNAL SELECTOR AND MEDICAL IMAGE FILING SYSTEM THEREWITH

(75) Inventor: Kazunori Abe, Saitama (JP)

(73) Assignee: Fujifilm Corporation, Tokyo (JP)

( * ) Notice: Subject to any disclaimer, the term of this patent is extended or adjusted under 35 U.S.C. 154(b) by 381 days.

(21) Appl. No.: 12/564,760

(22) Filed: Sep. 22, 2009

(65) Prior Publication Data

US 2010/0079586 A1 Apr. 1, 2010

(30) Foreign Application Priority Data

Sep. 30, 2008 (JP) ................. 2008-255787

(51) Int. Cl.
*A61B 1/04* (2006.01)
(52) U.S. Cl. ....................................... 348/75
(58) Field of Classification Search ............... 348/65–76
See application file for complete search history.

(56) References Cited

U.S. PATENT DOCUMENTS

2007/0167754 A1  7/2007 Okuno et al.
2008/0221447 A1  9/2008 Igarashi et al.
2009/0118614 A1*  5/2009 Sendai ........................... 600/437
2010/0002917 A1*  1/2010 Sakaida ........................ 382/128

FOREIGN PATENT DOCUMENTS

| EP | 1 690 497 A1 | 8/2006 |
| EP | 1 967 129 A1 | 9/2008 |
| JP | 10-211201 | 8/1998 |
| JP | 2004-358233 | 12/2004 |
| WO | WO 2008/001694 | * 1/2008 |

OTHER PUBLICATIONS

Extended European Search Report dated Dec. 1, 2009.

* cited by examiner

*Primary Examiner* — Larry Donaghue
(74) *Attorney, Agent, or Firm* — McGinn IP Law Group, PLLC

(57) ABSTRACT

A video signal selector has a selector switch for selectively outputting one of an endoscopic video signal and an ultrasonic video signal, and a selector control circuit for controlling the selector switch. The selector switch selects the endoscopic video signal by default. The selector control circuit switches the selector switch to the ultrasonic video signal in response to input of an ultrasonic image capture command for commanding to save an ultrasonic image.

15 Claims, 3 Drawing Sheets

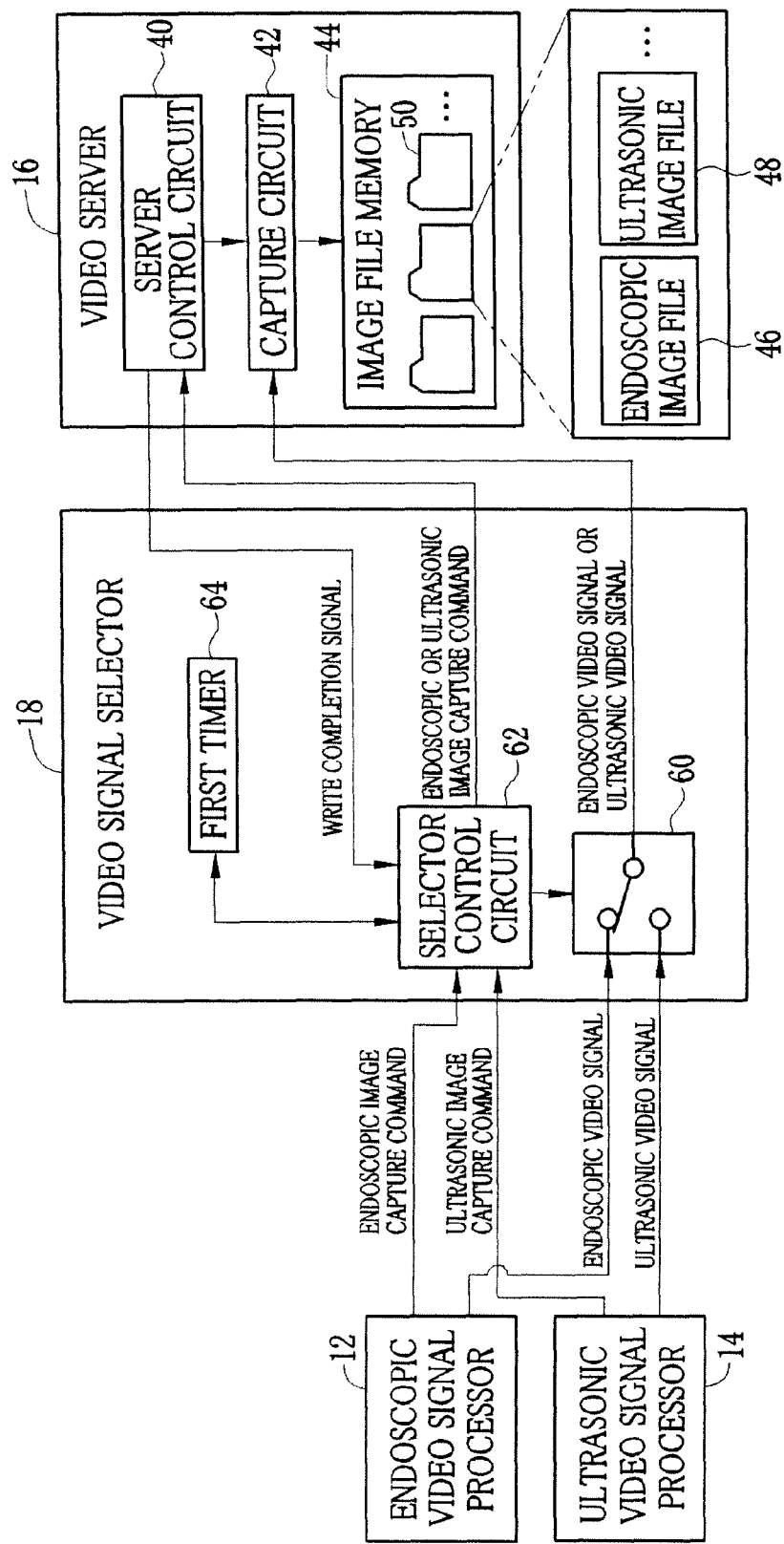

VIDEO SIGNAL SELECTOR AND MEDICAL IMAGE FILING SYSTEM THEREWITH

BACKGROUND OF THE INVENTION

1. Field of the Invention

The present invention relates to a video signal selector and a medical image filing system therewith, and particularly relates to the video signal selector that automatically selects one of an endoscopic video signal and another medical video signal such as an ultrasonic video signal and the medical image filing system therewith.

2. Description Related to the Prior Art

In endoscopy, a flexible slender tube of an electronic endoscope is introduced into patient's body from his/her mouth or the like to look inside the body. In recent years, endoscopic ultrasonography (EUS) is commonly known, in which an ultrasonic transducer provided at a distal end of the tube applies ultrasonic waves to an internal body part, and receives reflected waves therefrom to form an image. The EUS can visualize an inner wall of an organ in its thickness (penetration) direction. Accordingly, the EUS is preferably used in examination of, for example, the digestive system including esophagus and duodenum, for the purpose of precisely finding out the depth of a lesion such as cancer and ulcer cells.

A medical image filing system for the EUS is generally constituted of an ultrasonic endoscope, an endoscopic video signal processor, an ultrasonic video signal processor, a monitor and a video server. The ultrasonic endoscope has the ultrasonic transducer and an image sensor such as CCD at a distal end of an insert section. The endoscopic video signal processor produces an endoscopic video signal from a pickup signal of the image sensor. The ultrasonic video signal processor produces an ultrasonic video signal from a detection signal of the ultrasonic transducer. The monitor receives the endoscopic video signal and ultrasonic video signal, and selectively or simultaneously displays endoscopic video and ultrasonic video on its screen. The video server obtains the endoscopic or ultrasonic video signal, and saves part or whole of the signal as a still image or moving images. Instead of the ultrasonic endoscope, a combination of an ultrasonic probe and the electronic endoscope may be used. In this case, the ultrasonic probe is inserted into a medical instrument insertion port of the electronic endoscope, and protrudes from a distal end of an insert section to emit ultrasonic waves inside the patient's body.

In the medical image filing system, the video server requires two-channel input for the entry of both of the endoscopic and ultrasonic video signals. The video server, however, just has single channel input in most cases. Preparing a video server with the two-channel input brings about increase in equipment cost of a hospital.

Thus, a switch was conventionally provided between the video signal processors and the video server. In response to manual operation with a dial, button or the like, the switch selects one of the endoscopic video signal and ultrasonic video signal, and inputs the selected signal into the video server. Providing the switch enables the use of the conventional video server with the single-channel input, and hence prevents increase in equipment cost (refer to Japanese Patent Laid-Open Publication No. 10-211201).

In the above system, however, there was the possibility of human error, e.g. forgetting switching operation. For example, while the switch is selecting the endoscopic video signal, the ultrasonic video signal is never written into the video server even if an ultrasonic image capture command is issued. The human error causes mis-recording of the image. The recorded image is checked after completion of the examination, so that the mis-recording of the image results in re-examination.

SUMMARY OF THE INVENTION

An object of the present invention is to provide a video signal selector and a medical image filing system that can certainly prevent mis-recording of an image.

A video signal selector according to the present invention includes a selector switch for selecting one of a first output mode and a second output mode, and a selector control circuit for controlling the selector switch. The selector switch outputs an endoscopic video signal as an output video signal in the first output mode, and outputs another medical video signal as the output video signal in the second output mode. The endoscopic and medical video signals are inputted in parallel to the selector switch. The selector control circuit controls the selector switch so as to switch from the first output mode to the second output mode in response to a first image capture command for capturing an image from the medical video signal.

The selector control circuit further controls the selector switch so as to switch from the second output mode to the first output mode in response to a second image capture command. The first or second image capture command is issued in response to operation of a corresponding operating member.

The video signal selector has an input side and an output side. To the input side, an endoscopic video signal processor for producing the endoscopic video signal and a medical video signal processor for producing the medical video signal are connected. To the output side, an image server for storing an image is connected. The image server captures the image from the output video signal selected by the selector switch in response to the first or second image capture command.

The selector control circuit may send the first or second image capture command to the image server with a delay of predetermined time. The selector control circuit may control the selector switch so as to switch from the second output mode to the first output mode, when the image server has completed saving the image captured from the medical video signal.

An electronic endoscope is connected to the endoscopic video signal processor. An ultrasonic transducer array for taking an ultrasonic video signal as the medical video signal is connected to the medical video signal processor. The ultrasonic transducer array is fixedly or detachably attached to the electronic endoscope.

The selector control circuit may control the selector switch so as to select the first output mode by default. The selector control circuit may control the selector switch so as to switch over to the first output mode, when predetermined time has elapsed since the selector switch selected the second output mode. The predetermined time may be variable.

It is preferable that the selector control circuit refuse acceptance of the second image capture command, while the selector switch is in the second output mode.

A medical image filing system includes an endoscopic video signal processor for producing an endoscopic video signal, a medical video signal processor for producing another medical video signal, a video signal selector to which the endoscopic video signal processor and the medical video signal processor are connected, and an image server. The video signal selector includes a selector switch for selecting one of a first output mode and a second output mode, and a selector control circuit for controlling the selector switch. The selector switch outputs the endoscopic video signal as an output video signal in the first output mode, and outputs the medical video signal as the output video signal in the second output mode. The endoscopic video signal and the medical video signal are inputted in parallel to the selector switch. The selector control circuit controls the selector switch so as to switch from the first output mode to the second output mode in response to a first image capture command, and switch from the second output mode to the first output mode in response to a second image capture command. The image server captures an image from the output video signal, and saves the image therein in response to the first or second image capture command.

The first or second image capture command is issued in response to operation of a corresponding operating member. An electronic endoscope may be connected to the endoscopic video signal processor. An ultrasonic transducer array for taking an ultrasonic video signal as the medical video signal may be connected to the medical video signal processor. The ultrasonic transducer array is fixedly or detachably attached to the electronic endoscope. The image is a still image or moving images.

According to the present invention, since the selector switch is automatically switched over in response to the first or second image capture command, it is possible to certainly prevent human error such as forgetting switching operation.

BRIEF DESCRIPTION OF THE DRAWINGS

For more complete understanding of the present invention, and the advantage thereof, reference is now made to the following descriptions taken in conjunction with the accompanying drawings, in which:

FIG. 3 is a block diagram of a video signal selector and a video server according to a second embodiment.

DESCRIPTION OF THE PREFERRED EMBODIMENTS

Figure 1:
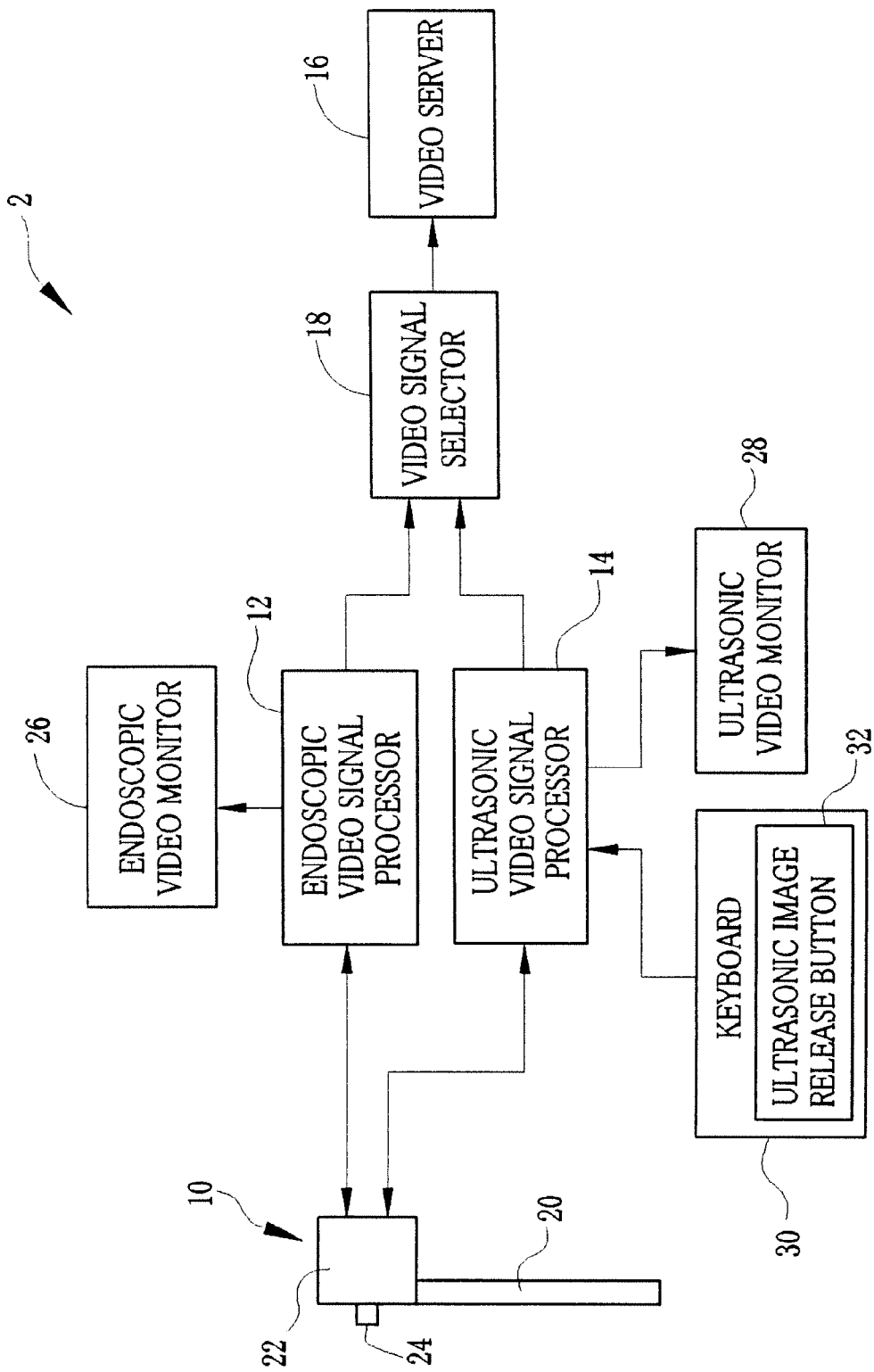
FIG. 1 is a block diagram of an image filing system for an ultrasonic endoscope.

As shown in FIG. 1, a medical image filing system 2 for endoscopic ultrasonography (EUS) is constituted of an ultrasonic endoscope 10 for taking a video inside a human body cavity, an endoscopic video signal processor 12 for producing an endoscopic video signal, an ultrasonic video signal processor 14 for producing an ultrasonic video signal, an video server 16, and a video signal selector 18. The video signal selector 18 selects one of the endoscopic video signal and ultrasonic video signal, and outputs the selected signal to the video server 16. The video server 16 captures an endoscopic or ultrasonic image from the inputted video signal, and saves the image therein.

The ultrasonic endoscope 10 has an insert section 20 to be inserted into the human body cavity, and a handling section 22 coupled to a proximal end of the insert section 20. To the handling section 22, a universal cord is connected. An end of the universal cord is provided with a multi-connector that is connected to both of the endoscopic video signal processor 12 and ultrasonic video signal processor 14. Thus, the ultrasonic endoscope 10 is detachably connected to the endoscopic video signal processor 12 and ultrasonic video signal processor 14 via the multi-connector. To the ultrasonic endoscope 10, a light source unit is also connected for supplying light to the inside of the body cavity.

The flexible insert section 20 has a tubular shape, round in cross section. The insert section 20 has a CCD for optical photography and an ultrasonic transducer array for the EUS at its distal end. A balloon that is inflatable with water, air or the like is also attached to the distal end of the insert section 20. The balloon is used in the case of, for example, impounding water in the body cavity to prevent attenuation of ultrasonic waves.

On the handling section 22, an endoscopic image release button 24 or first operating member is provided for issue of an endoscopic image capture command to the video server 16. The endoscopic image release button 24 is electrically connected to the endoscopic video signal processor 12 through the universal cord and the like.

The endoscopic video signal processor 12 sends a drive signal to the ultrasonic endoscope 10, and actuates the CCD in the ultrasonic endoscope 10. The endoscopic video signal processor 12 receives an analog pickup signal from the CCD, and produces an endoscopic video signal by applying A/D conversion and various video processing to the pickup signal. The endoscopic video signal is outputted to the video signal selector 18.

An endoscopic video monitor 26 is connected to the endoscopic video signal processor 12. The endoscopic video signal processor 12 converts the endoscopic video signal into a component or composite video signal compliant with the endoscopic video monitor 26, and outputs the video signal to the endoscopic video monitor 26. Accordingly, the endoscopic video monitor 26 displays a live endoscopic video image on its screen.

In response to a press of the endoscopic image release button 24, the endoscopic video signal processor 12 issues the endoscopic image capture command to the video signal selector 18.

The ultrasonic video signal processor 14 feeds the ultrasonic endoscope 10 with exciting pulses (pulse voltage) for making the ultrasonic transducer array produce ultrasonic waves. The ultrasonic transducer array applies the ultrasonic waves to an inner wall of an organ inside the body cavity, and receives reflected waves therefrom. The reflected waves are converted into an electric detection signal by piezoelectric elements in the ultrasonic transducer array, and the detection signal is outputted to the ultrasonic video signal processor 14. The ultrasonic video signal processor 14 applies A/D conversion and various video processing to the detection signal, and produces an ultrasonic video signal. The ultrasonic video signal is outputted to the video signal selector 18.

An ultrasonic video monitor 28 is connected to the ultrasonic video signal processor 14. The ultrasonic video signal processor 14 converts the ultrasonic video signal into a component or composite video signal compliant with the ultrasonic video monitor 28, and outputs the video signal to the ultrasonic video monitor 28. Accordingly, the ultrasonic video monitor 28 displays a live ultrasonic video image on its screen.

To the ultrasonic video signal processor 14, a keyboard 30 is connected for entry of various operation commands into the ultrasonic video signal processor 14. The keyboard 30 is provided with an ultrasonic image release button 32 or second operating member for issue of an ultrasonic image capture command to the video server 16. In response to a press of the ultrasonic image release button 32, the ultrasonic video signal processor 14 outputs the ultrasonic image capture command to the video signal selector 18.

Figure 2:
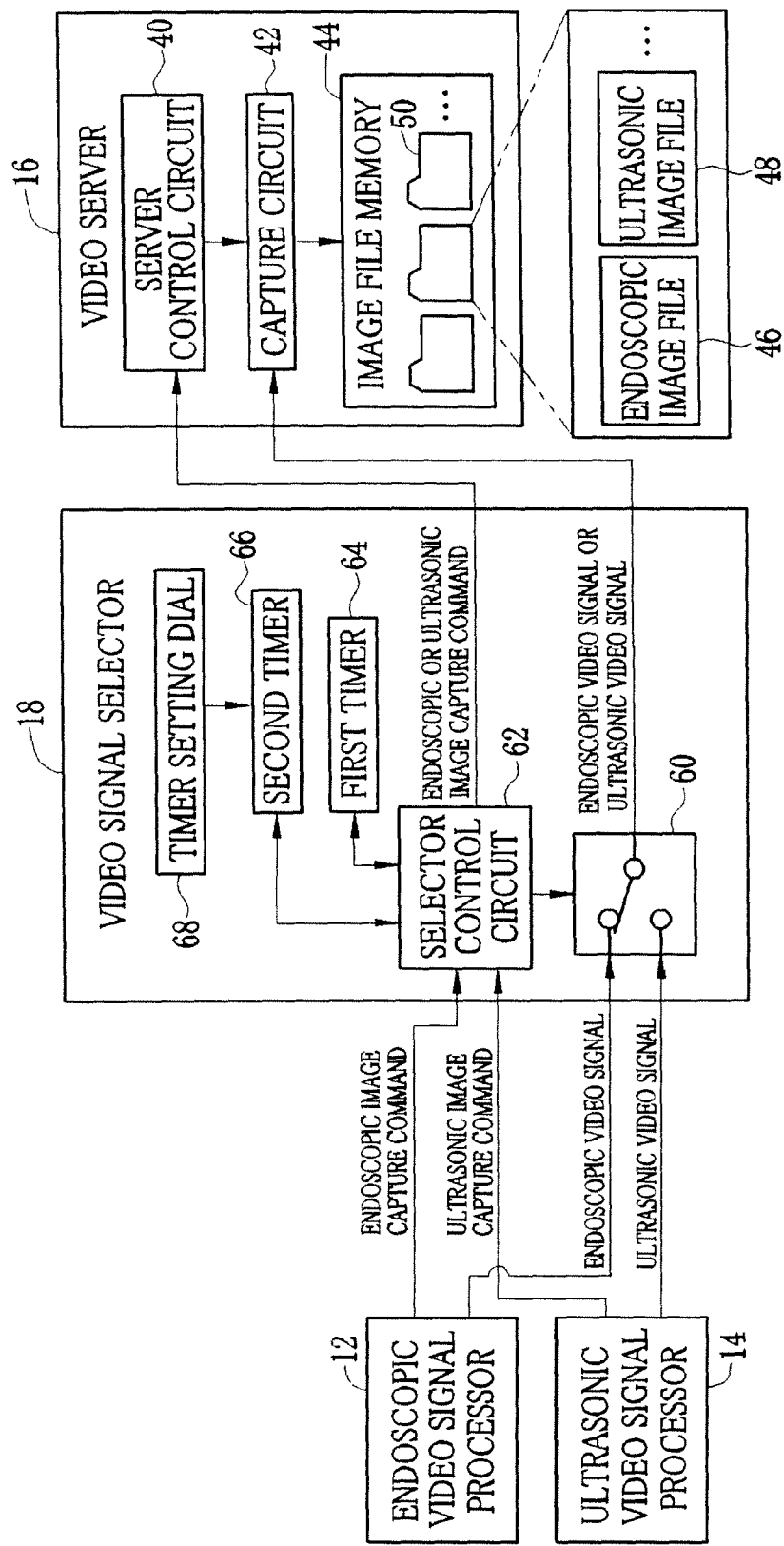
FIG. 2 is a block diagram of a video signal selector and a video server according to a first embodiment.

As shown in FIG. 2, the video server 16 is provided with a server control circuit 40, a capture circuit 42, and an image file memory 44. The server control circuit 40 controls the entire video server 16. The capture circuit 42 receives the endoscopic or ultrasonic video signal from the video signal selector 18. The capture circuit 42 extracts data of a single endoscopic still image from the endoscopic video signal, and generates an endoscopic image file 46 in response to a command from the server control circuit 40. Or, the capture circuit 42 extracts data of a single ultrasonic still image from the ultrasonic video signal, and generates an ultrasonic image file 48.

Upon starting an examination, a folder 50 is created in the image file memory 44. The image file memory 44 has a plurality of folders 50 that are created on an examination basis. The capture circuit 42 generates the endoscopic and ultrasonic image files 46 and 48, and sequentially writes the files 46 and 48 into the corresponding folder 50. Accordingly, a number of endoscopic and ultrasonic image files 46 and 48 taken in the single examination are stored in the folder 50 of the image file memory 44 in proper time sequence.

The video signal selector 18 is provided with a selector switch 60 or signal switching device, a selector control circuit 62 for controlling the selector switch 60, a first timer 64, a second timer 66, and a timer setting dial 68 for setting the second timer 66.

The endoscopic video signal and ultrasonic video signal are inputted into the selector switch 60 from the endoscopic video signal processor 12 and ultrasonic video signal processor 14, respectively. The selector switch 60 selects one of the endoscopic video signal and ultrasonic video signal in response to a command from the selector control circuit 62, and outputs the selected signal to the capture circuit 42. As the selector switch 60, a well-known switching device such as relay and multiplexer is available.

To the selector control circuit 62, the endoscopic image capture command and ultrasonic image capture command are inputted. The selector control circuit 62 controls the selector switch 60 in response to the input of each capture command.

The selector control circuit 62 is connected to the server control circuit 40 of the video server 16. Upon receiving the endoscopic or ultrasonic image capture command, the selector control circuit 62 transfers the inputted capture command to the server control circuit 40, besides control of the selector switch 60. The server control circuit 40 commands the capture circuit 42 to get the endoscopic or ultrasonic image in response to the capture command from the selector control circuit 62.

The selector control circuit 62 controls the selector switch 60 so as to select the endoscopic video signal by default, and switch to the ultrasonic video signal only when the ultrasonic image capture command is inputted. When the ultrasonic video signal processor 14 issues the ultrasonic image capture command by a press of the ultrasonic image release button 32, the selector switch 60 is switched from the endoscopic video signal to the ultrasonic video signal in response to a selection switch command from the selector control circuit 62. Accordingly, the ultrasonic video signal is outputted to the capture circuit 42.

After issue of the selection switch command to the selector switch 60, the selector control circuit 62 actuates the first timer 64 to start counting. While the first timer 64 is counting a predetermined time, the selector control circuit 62 holds the ultrasonic image capture command. The instant when the count of the first timer 64 has reached the predetermined time, the selector control circuit 62 outputs the ultrasonic image capture command to the server control circuit 40. The server control circuit 40 commands the capture circuit 42 to get the ultrasonic image in response to the ultrasonic image capture command. The capture circuit 42 extracts the ultrasonic image data from the ultrasonic video signal outputted from the selector switch 60, and generates the ultrasonic image file 48. Then, the capture circuit 42 writes the ultrasonic image file 48 into the appropriate folder 50 in the image file memory 44.

The selector control circuit 62, as described above, outputs the ultrasonic image capture command to the server control circuit 40 with a delay of predetermined time. Generally speaking, an output signal becomes unstable immediately after switching the selector switch 60, and it takes some time to stabilize the signal. Accordingly, if the ultrasonic image capture command is outputted immediately after switching the selector switch 60, the capture circuit 42 may read the unstable video signal and generate an abnormal ultrasonic image file 48.

The selector control circuit 62 delays the output of the ultrasonic image capture command in order to prevent the generation of the strange ultrasonic image file 48. The first timer 64 is set at, for example, 0.3 seconds, in consideration of time for stabilization of the selector switch 60. The first timer 64 may be set at appropriate time in accordance with the performance of the selector switch 60.

After the output of the ultrasonic image capture command to the server control circuit 40, the selector control circuit 62 actuates the second timer 66. When the count of the second timer 66 has reached a predetermined time, the selector control circuit 62 commands the switching of the selector switch 60. Thus, the selector switch 60 is switched from the ultrasonic video signal to the endoscopic video signal.

The second timer 66 is set at an appropriate time in accordance with time that the capture circuit 42 normally writes the ultrasonic image file 48 into the image file memory 44. The set time varies depending on the performance of the connected video server 16. Accordingly, the set time of the second timer (time to keep selecting the ultrasonic video signal) is variable by the timer setting dial 68. Therefore, since the selector switch 60 is not switched while the capture circuit 42 writes the ultrasonic image file 48 into the image file memory 44, it is possible to prevent abnormal write of the ultrasonic image file 48.

The timer setting dial 68 is a well-known operating part such as sliding knob or dial. The timer setting dial 68 is provided on a surface of a case of the video signal selector 18 for easy setting by a doctor. When a different model of video server 16 is connected to the video signal selector 18, the doctor operates the timer setting dial 68 to set the second timer 66 in accordance with the performance of the video server 16. The second timer 66 is set variably between, for example, 0.1 seconds and 1.0 second by the timer setting dial 68.

When the endoscopic image release button 24 is accidentally pressed during write of the ultrasonic image file 48, and the selector switch 60 is switched from ultrasonic video signal to the endoscopic video signal, an abnormal ultrasonic image file 48 may be written, as with the above. Accordingly, the selector control circuit 62 does not accept the endoscopic image capture command from the ultrasonic video signal processor 12 while the second timer 66 operates.

As described above, the selector control circuit 62 makes the selector switch 60 select the endoscopic video signal by default. When the endoscopic image capture command is inputted from the endoscopic video signal processor 12 in response to a press of the endoscopic image release button 24, the selector control circuit 62 immediately transfers the endoscopic image capture command to the server control circuit 40, without switching of the selector switch 60 and actuation of the first timer 64.

Upon inputting the endoscopic image capture command, the server control circuit 40 commands the capture circuit 42 to carry out image capture operation. The capture circuit 42 generates the endoscopic image file 46 from the endoscopic video signal outputted from the selector switch 60. Then, the capture circuit 42 writes the endoscopic image file 46 into the appropriate folder 50 of the image file memory 44.

Next, the case of observing a lesion in the esophagus will be described. First, the doctor sets up every part as shown in FIG. 1, and turns the power on. When the every part has actuated, live video is displayed on the endoscopic and ultrasonic video monitors 26 and 28 (video outside the body cavity at this time, because the insert section 22 has not been inserted yet). The selector control circuit 62 commands the selector switch 60 or signal switching device to select the endoscopic video signal, so that the endoscopic video signal is outputted to the capture circuit 42.

When the endoscopic and ultrasonic video is displayed, the doctor checks the operation of individual parts. At this time, the doctor operates the timer setting dial 68 as necessary, in order to appropriately set the second timer 66 in accordance with the video server 16. Then, the doctor presses an examination start button, which is provided on the endoscopic video signal processor 12, to start an examination. Upon starting the examination, the folder 50 for storing images is newly created in the image file memory 44.

Then, the doctor introduces the insert section 20 of the ultrasonic endoscope 10 into the patient's body cavity while looking at the live endoscopic video on the endoscopic video monitor 26, and starts observing inside the body cavity. If the doctor has found out a lesion in the esophagus in the endoscopic video, the balloon provided at the distal end of the insert section 20 is inflated by a syringe pump or the like in order to block the esophagus at a point slightly beyond the lesion.

After that, the doctor adjusts the position of the ultrasonic endoscope 10 so that the lesion is displayed on the endoscopic video monitor 26, and presses the endoscopic image release button (freeze button) 24. Upon pressing the endoscopic image release button 24, the endoscopic video signal processor 12 issues the endoscopic image capture command. The endoscopic image capture command is transmitted to the server control circuit 40 through the selector control circuit 62. In response to the endoscopic image capture command, the server control circuit 40 commands the capture circuit 42 to capture the endoscopic image from the endoscopic video signal outputted from the selector switch 60. The capture circuit 42 generates the endoscopic image file 46 having a single frame of a still image from the endoscopic video signal. Accordingly, the endoscopic image file 46 that depicts the surface of the lesion in the esophagus is saved in the folder 50.

After obtaining the endoscopic image file 46 of the lesion, water is discharged from the distal end of the insert section 20 to fill the esophagus, which is blocked by the balloon, with the water for preventing attenuation of the ultrasonic waves. Then, the doctor observes the ultrasonic video on the ultrasonic video monitor 28, and presses the ultrasonic image release button (freeze button) 32 at appropriate timing to obtain a desired ultrasonic image. When the ultrasonic image release button 32 is pressed, the ultrasonic video may be frozen and the ultrasonic image to be saved may be displayed on the ultrasonic video monitor 28 for doctor's convenience.

In response to the press of the ultrasonic image release button 32, the ultrasonic video signal processor 14 issues and outputs the ultrasonic image capture command to the selector control circuit 62. In response to the ultrasonic image capture command, the selector control circuit 62 switches the selector switch 60 from the endoscopic video signal to the ultrasonic video signal. The automatic switching of the selector switch 60 in response to the press of the ultrasonic image release button 32, as described above, certainly prevents human error, namely forgetting to operate the selector switch 60. There is no need for manual switching operation, and hence the doctor can concentrate on the examination.

When the ultrasonic image capture command is inputted, the selector control circuit 62 actuates the first timer 64, in addition to commanding the switching of the selector switch 60. Then, the selector control circuit 62 delays the ultrasonic image capture command by the predetermined time by the first timer 64, and outputs the ultrasonic image capture command to the server control circuit 40. In response to the ultrasonic image capture command, the server control circuit 40 commands the capture circuit 42 to get the ultrasonic image from the ultrasonic video signal outputted from the selector switch 60. The capture circuit 42 generates the ultrasonic image file 48, which has a single frame of ultrasonic still image, from the ultrasonic video signal. Accordingly, the ultrasonic image file 48 that depicts tissue of the lesion under the inner wall of the esophagus is saved in the folder 50. Delaying the ultrasonic image capture command, as described above, can prevent the capture circuit 42 from capturing the image from the unstable ultrasonic video signal that is outputted immediately after the switching of the selector switch 60.

After outputting the ultrasonic image capture command to the server control circuit 40 with a delay, the selector control circuit 62 actuates the second timer 66. The second timer 66 starts counting time set by the timer setting dial 68. When the count of the second timer 66 has reached the set time, the selector control circuit 62 commands the selector switch 60 to switch from the ultrasonic video signal to the endoscopic video signal.

After the ultrasonic image file 48 is saved, the water in the esophagus is removed by suction. Then, the doctor presses the endoscopic image release button 24 again to obtain another endoscopic image file 46. At this time, the selector control circuit 62 does not accept the endoscopic image capture command that is inputted before the switching of the selector switch 60 to the endoscopic video signal. Therefore, it is possible to prevent the switching of the selector switch 60 while the capture circuit 42 is writing the ultrasonic image file 48 on the image file memory 44.

After saving the second endoscopic image file 46, the balloon is deflated. Processing for the single lesion has been completed now. The doctor observes inside the body cavity along a route leading to the stomach and duodenum, and repeats the above processing whenever a lesion is found out. When the examination has been completed, the insert section 20 of the ultrasonic endoscope 10 is pulled out of the body cavity. The doctor presses an examination end button provided on the endoscopic video signal processor 12 to command the individual parts of the image filing system 2 to end the examination.

The above image filing system 2 for the ultrasonic endoscope 10 has the second timer 66 and the timer setting dial 68. The second timer 66 is set by the timer setting dial 68 in accordance with time required by the capture circuit 42 for normally writing the ultrasonic image file 48 on the image file memory 44. When the count of the second timer 66 has reached the set time, the selector switch 60 is switched from the ultrasonic video signal to the endoscopic video signal.

Instead of the above, as shown in FIG. 3, a write completion signal that indicates normal completion of write of the ultrasonic image file 48 may be inputted from the server control circuit 40 of the video server 16 to the selector control circuit 62 of the video signal selector 18. Upon receiving the write completion signal, the selector switch 60 is switched from the ultrasonic video signal to the endoscopic video signal.

In the foregoing embodiments, the selector switch 60 selects the endoscopic video signal by default, and selects the ultrasonic video signal only when the ultrasonic image capture command is inputted. However, the selector switch 60 or signal switching device may select the endoscopic video signal in response to input of the endoscopic image capture command, and select the ultrasonic video signal in response to input of the ultrasonic image capture command.

Instead of the ultrasonic endoscope 10, an ultrasonic probe that is inserted into a medical instrument insertion port of an electronic endoscope may be used.

The foregoing embodiments deal with two types of medical video signals, that is, the endoscopic video signal and ultrasonic video signal. However, instead of the ultrasonic video signal, is available a video signal of, for example, an endoscope with an ultrasmall diameter (so-called baby scope) that is inserted into the medical instrument insertion port of the electronic endoscope and used for observation of the biliary tract or the like.

The image filing system 2 according to the foregoing embodiments captures the still image from the video signal, and generates the image files 46 and 48. The present invention, however, is applicable to an image filing system that captures moving images and generates a video file.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A video signal selector comprising:
   a selector switch for selecting one of a first output mode and a second output mode, for outputting an endoscopic video signal as an output video signal in said first output mode, and outputting another medical video signal as said output video signal in said second output mode, said endoscopic video signal and said medical video signal being inputted in parallel with one another to said selector switch; and
   a selector control circuit for controlling said selector switch so as to switch from said first output mode to said second output mode in response to a first image capture command for capturing an image from said medical video signal,
   wherein said selector control circuit further controls said selector switch so as to switch from said second output mode to said first output mode in response to a second image capture command,
   wherein said video signal selector has an input side and an output side, to said input side an endoscopic video signal processor for producing said endoscopic video signal and a medical video signal processor for producing said medical video signal are connected, to said output side an image server for storing an image is connected, and said image server captures said image from said output video signal selected by said selector switch in response to said first image capture command or said second image capture command,
   wherein said selector control circuit controls said selector switch so as to switch from said second output mode to said first output mode, when said image server has completed saving said image captured from said medical video signal, and
   wherein said selector control circuit refuses acceptance of said second image capture command, while said selector switch is in said second output mode.

2. The video signal selector according to claim 1, wherein said first image capture command or said second image capture command is issued in response to operation of a corresponding operating member.

3. The video signal selector according to claim 1, wherein said selector control circuit sends said first image capture command or said second image capture command to said image server with a delay of predetermined time.

4. The video signal selector according to claim 1, wherein an electronic endoscope is connected to said endoscopic video signal processor, an ultrasonic transducer array for taking an ultrasonic video signal as said medical video signal is connected to said medical video signal processor, and said ultrasonic transducer array is fixedly or detachably attached to said electronic endoscope.

5. The video signal selector according to claim 2, wherein said selector control circuit controls said selector switch so as to select said first output mode by default.

6. The video signal selector according to claim 5, wherein said selector control circuit controls said selector switch so as to switch over to said first output mode, when predetermined time has elapsed since said selector switch selected said second output mode.

7. The video signal selector according to claim 6, wherein said predetermined time is variable.

8. The video signal selector according to claim 1, wherein the selector control circuit is configured to automatically switch said selector switch from said first output mode to said second output mode.

9. The video signal selector according to claim 5, wherein said selector switch switches to said second output mode only in response to said first image capture command.

10. The video signal selector according to claim 4, wherein said electronic endoscope includes an ultrasonic image operating mechanism, and
    wherein when the ultrasonic image operating mechanism is operated, the selector switch automatically switches to said second output mode.

11. The video signal selector according to claim 1, wherein the selector switch is prevented from switching while an image, captured in said second output mode, is written to memory.

12. A medical image filing system comprising:
    an endoscopic video signal processor for producing an endoscopic video signal;
    a medical video signal processor for producing another medical video signal;
    a video signal selector to which said endoscopic video signal processor and said medical video signal processor are connected, comprising;
    (A) a selector switch for selecting one of a first output mode and a second output mode, for outputting said endoscopic video signal as an output video signal in said first output mode, and outputting said medical video signal as said output video signal in said second output mode, said endoscopic video signal and said medical video signal being inputted in parallel with one another to said selector switch; and
    (B) a selector control circuit for controlling said selector switch so as to switch from said first output mode to said second output mode in response to a first image capture command, and switch from said second output mode to said first output mode in response to a second image capture command; and an image server for capturing an image from said output video signal and saving said image therein in response to said first image capture command or said second image capture command, wherein said selector control circuit further controls said selector switch so as to switch from said second output mode to said first output mode in response to said second image capture command, wherein said video signal selector has an input side and an output side, to said input side said endoscopic video signal processor for producing said endoscopic video signal and said medical video signal processor for producing said medical video signal are connected, to said output side said image server for storing the image is connected, and said image server captures said image from said output video signal selected by said selector switch in response to said first image capture command or said second image capture command, wherein said selector control circuit controls said selector switch so as to switch from said second output mode to said first output mode, when said image server has completed saving said image captured from said medical video signal, and wherein said selector control circuit refuses acceptance of said second image capture command, while said selector switch is in said second output mode.

13. The medical image filing system according to claim 12, wherein said first image capture command or said second image capture command is issued in response to operation of a corresponding operating member.

14. The medical image filing system according to claim 13, wherein an electronic endoscope is connected to said endoscopic video signal processor, an ultrasonic transducer array for taking an ultrasonic video signal as said medical video signal is connected to said medical video signal processor, and said ultrasonic transducer array is fixedly or detachably attached to said electronic endoscope.

15. The medical image filing system according to claim 14, wherein said image comprises is a still image or moving image.

* * * * *